US006561186B2

(12) United States Patent
Casper et al.

(10) Patent No.: US 6,561,186 B2
(45) Date of Patent: *May 13, 2003

(54) DRY POWDER MEDICAMENT INHALATOR HAVING AN INHALATION-ACTIVATED FLOW DIVERTING MEANS FOR TRIGGERING DELIVERY OF MEDICAMENT

(75) Inventors: Robert A. Casper, Raleigh, NC (US); Frank A. Leith, Chapel Hill, NC (US); David L. Gardner, Chapel Hill, NC (US); John M. Snow, Raleigh, NC (US); Zachary W. Lyon, Raleigh, NC (US); David S. Farrar, Fuquay-Varina, NC (US)

(73) Assignee: Innovative Devices, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/995,923

(22) Filed: Nov. 27, 2001

(65) Prior Publication Data

US 2002/0033176 A1 Mar. 21, 2002

Related U.S. Application Data

(62) Division of application No. 09/492,714, filed on Jan. 27, 2000, which is a division of application No. 09/042,656, filed on Mar. 17, 1998, now Pat. No. 6,209,583, which is a continuation-in-part of application No. 08/823,139, filed on Mar. 25, 1997, now Pat. No. 5,823,183, which is a continuation of application No. 08/690,989, filed on Aug. 1, 1996, now Pat. No. 5,692,496.
(60) Provisional application No. 60/001,786, filed on Aug. 2, 1995.

(51) Int. Cl.$^7$ .................... A61M 15/00; A61M 16/00; B05D 7/14; B65D 83/06
(52) U.S. Cl. .................... 128/203.15; 128/200.24; 128/203.12; 128/203.21

(58) Field of Search ................. 128/203.15, 203.12, 128/203.21, 200.24; 604/58

(56) References Cited

U.S. PATENT DOCUMENTS

| 3,807,400 A | 4/1974 | Cocozza |
| 3,906,950 A | 9/1975 | Cocozza |

(List continued on next page.)

FOREIGN PATENT DOCUMENTS

| DE | 40 20 571 A1 | 1/1992 |
| DE | 4133 274 | 2/1993 |
| EP | 0 211595 A2 | 2/1987 |
| EP | 0 455 463 A1 | 4/1991 |
| EP | 0 467 172 A1 | 7/1991 |
| GB | 2 129 691 B | 5/1984 |

(List continued on next page.)

*Primary Examiner*—Weilun Lo
*Assistant Examiner*—Darwin P Erezo
(74) *Attorney, Agent, or Firm*—Morriss, Bateman, O'Bryant & Compagni

(57) ABSTRACT

An inhalation-activated inhalator having a primary inhalation passage and a secondary inhalation passage disposed in communication with the primary inhalation passage and a source of medicament. The primary inhalation passage has airflow inhibiting mechanism connected to a blocking plate positioned to selectively block fluid flow in the secondary inhalation passage. As the user's inhalation reaches a defined rate, the flow inhibiting mechanism restricts flow through the primary inhalation passage and moves the blocking plate to enable airflow through the secondary passage. Thus, as the user achieves a desired inhalation rate, the medicament is provided through the secondary inhalation passage, thereby optimizing the delivery of medicament to the lungs.

40 Claims, 10 Drawing Sheets

U.S. PATENT DOCUMENTS

| | | |
|---|---|---|
| 3,921,637 A | 11/1975 | Bennie et al. |
| 3,991,761 A | 11/1976 | Cocozza |
| 4,013,075 A | 3/1977 | Cocozza |
| 4,627,432 A | 12/1986 | Newell et al. |
| 4,664,107 A | 5/1987 | Wass |
| 4,667,668 A | 5/1987 | Wetterlin |
| 4,668,218 A | 5/1987 | Virtanen |
| 4,778,054 A | 10/1988 | Newell et al. |
| 4,805,811 A | 2/1989 | Wetterlin |
| 4,811,731 A | 3/1989 | Newell et al. |
| 5,033,463 A | 7/1991 | Cocozza |
| 5,161,524 A | 11/1992 | Evans |
| 5,201,308 A | 4/1993 | Newhouse |
| 5,320,714 A | 6/1994 | Brendel |
| 5,347,999 A | 9/1994 | Poss et al. |
| 5,388,572 A | 2/1995 | Mulhauser et al. |
| 5,408,994 A | 4/1995 | Wass et al. |
| 5,437,271 A | 8/1995 | Hodson et al. |
| 5,447,151 A | 9/1995 | Bruna et al. |
| 5,482,032 A | 1/1996 | Smith et al. |
| 5,483,954 A | 1/1996 | Mecikalski |
| 5,529,059 A | 6/1996 | Armstrong et al. |
| 5,692,496 A | 12/1997 | Casper et al. |
| 5,740,794 A | 4/1998 | Smith et al. |
| 5,823,183 A * | 10/1998 | Casper et al. .......... 128/203.15 |
| 5,988,163 A * | 11/1999 | Casper et al. .......... 128/203.15 |
| 6,209,538 B1 * | 4/2001 | Casper et al. .......... 128/203.15 |

FOREIGN PATENT DOCUMENTS

| | | |
|---|---|---|
| GB | 2 129 691 A | 5/1984 |
| GB | 2 142 246 A | 1/1985 |
| GB | 2 142 246 B | 1/1985 |
| GB | 2165159 A | 4/1986 |
| WO | WO 90/13328 | 11/1990 |
| WO | WO 93/12831 | 12/1992 |
| WO | WO 99/06092 | 2/1999 |
| WO | WO 99/47199 | 9/1999 |

* cited by examiner

DRY POWDER MEDICAMENT INHALATOR HAVING AN INHALATION-ACTIVATED FLOW DIVERTING MEANS FOR TRIGGERING DELIVERY OF MEDICAMENT

RELATED APPLICATIONS

This application is a divisional application of U.S. application Ser. No. 09/492,714, filed Jan. 27, 2000, which is a divisional application of U.S. application Ser. No. 09/042,656, filed Mar. 17, 1998, now U.S. Pat. No. 6,209,583, which is a continuation in part of U.S. application Ser. No. 08/823,139, filed Mar. 25, 1997, now U.S. Pat. No. 5,823,183, which is a continuation of U.S. application Ser. No. 08/690,989, filed Aug. 1, 1996, now U.S. Pat. No. 5,692,496, which claimed benefit of an application filed under 35 U.S.C. §111(a) for an invention which was disclosed in Provisional Application Serial No. 60/001,786, filed under 35 U.S.C. §111(b) on Aug. 2, 1995.

FIELD OF THE INVENTION

The present invention relates to an improved medicament inhalator. More particularly, the present invention relates to a dry powder medicament inhalator usable by asthmatics and the like in such a manner to facilitate proper deposition of the medicament in the lungs. By inhaling on a mouthpiece, a prescribed dosage of medicament becomes available to the patient during the proper phase of inspiration to maximize deposition of the medicament in the lungs of the user.

STATE OF THE ART

The widespread existence of asthma and other respiratory disorders which inhibit proper breathing has lead to the development of numerous medications which can be used to open restricted breathing passages and to enable the user to breathe more freely. Some asthmatics suffer from only occasional attacks. Other asthmatics suffer from attacks which are relatively minor and do not cause a serious inconvenience. For others, however, breathing is a constant struggle which would be nearly impossible without the appropriate medication. These medications may be in either dry or liquid form, depending on the type of medication.

There are essentially two types of inhalation devices currently available in the marketplace for the administration of a medicament to the lungs. The predominant inhalation device is a pressurized, metered dose inhaler containing a suspension of drug in a pharmaceutically inert liquid propellant, e.g., chlorofluorocarbons or fluorocarbons. Inhalation devices of this type are well known in the art and are commonly used.

These propellant-based inhalation devices have the advantage of consistently delivering a predetermined dose of medication form the aerosol canister. However, the drug particles are propelled at high velocity from the inhalation device. A significant quantity of the medication impacts tissue in the mouth or throat of the patient, becoming unavailable for deposition in the lungs. Further, growing concern over the link between depletion of atmospheric ozone and chlorofluorocarbon propellants has focused attention on the development of alternative means of delivering medication to the lungs, including the development of dry powder inhalation systems.

Dry powder inhalers represent the second major type of inhalation devices. Dry powder inhaler devices known to the applicants and existing in the marketplace utilize the patient's inhaled breath as a vehicle to transport the dry powder drug to the lungs. Presently there are four principal methods in use to provide fine particulate powder to the lungs without the use of chlorofluorocarbons or other propellants.

The first method available relies on the use of a hard gelatin capsule which contains a premeasured dose of therapeutically active material and an inhalator device for use with the capsule. The capsule is placed in the inhalator device which serves to open or perforate the capsule, exposing the dose of medicament. The medicament is removed from the capsule by the vacuum action created when the patient inhales through the mouthpiece of the device, and is entrained in the inspired air stream for transport to the patient's lungs. The empty capsule is removed from the inhalation device after each use.

Inhalators using this type of capsule technology are described in U.S. Pat. No. 3,807,400 (Cocozza); U.S. Pat. No. 3,906,950 (Cocozza); U.S. Pat. No. 3,991,761 (Cocozza) and U.S. Pat. No. 4,013,075 (Cocozza). The intent in each of these devices is to remove all of the powdered medicament from the interior of the capsule. However, it has been found that the air stream generated by the patient is typically insufficient to accomplish complete removal of medicament from the capsule. This may be especially true for a patient having reduced inhalation ability due to an asthma attack. Further, gelatin capsules are affected by relative humidity during storage and may become hydrated in moist environments. Hydration results in poor opening of the capsule and agglomeration of the powder contents, or dehydrated, resulting in brittle fracture of the capsule, potentially making fine gelatin fragments available for inhalation or compromising dosing due to electrostatic attraction of medicament to the capsule surfaces.

A second method for delivery of dry powder medicaments relies on providing a package containing multiple doses of medicament, each contained in a sealed blister. The package is used in conjunction with a specially designed inhalation device which provides a means of attachment for the package and perforation of an individual blister by the patient prior to the inhalation of its contents. Delivery systems of this type are described in EPO Patent Application Publication No. 0 211 595 A2 (Newell et al.); EPO Patent Application Publication No. 0 455 463 A1 (Velasquez et al.); and EPO Patent Application Publication No. 0 467 172 A1 (Cocozza et al.). As the patient inhales, a portion of the inhaled air stream flows continuously through the perforated blister entraining the medicament and providing for inclusion of the medicament in the inspired breath. Delivery of medicament to the patient's inspired air stream begins as sufficient flow develops through the blister for removal of the medicament. No means is provided by which the point or rate of delivery of medicament to the patient is controlled.

A third method for delivery of dry powder medicaments involves the use of a device equipped with a drug reservoir containing sufficient medicament for a much larger number of doses. The Draco TURBUHALER® is an example of this type of device and is described in detail in U.S. Pat. No. 4,688,218 (Virtanen); U.S. Pat. No. 4,667,668 (Wetterlin); and U.S. Pat. No. 4,805,811 (Wetterlin). The device provides a means for withdrawing a dose of medicament from the reservoir and presenting the withdrawn dose for inhalation by the patient. As the patient inhales through the mouthpiece of the device, the medicament contained in perforations in a dosing plate is entrained in the inspired air and flows through a conduit or conduits. The conduits serve as a vortex creating a means for breaking up powder agglomerates before the medicament becomes available to the patient. Moisture ingress in the reservoir results in agglomeration of the powder contents, compromising dosing due to retention of powder in the perforations in the dosing plate and potentially inadequate breakup of particulates in the inspired air stream.

A fourth method for delivery of dry powder medicaments involves the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device. Devices of this general type are described in PCT WO 93/12831 (Zirerenberg et al.); German Patent No. DE 4133274 A1 (Kühnel et al.); German Patent No. DE 4020571 A1 (Hochrainer et al.); and U.S. Pat. No. 5,388,572 (Mulhauser et al.). The incorporation of a piston system, in each case, adds to the complexity of the inhalation device, both in terms of use by the patient and device manufacturability.

Thus, there is a need for an improved medicament inhalator wherein the availability of the medicament is controlled to ensure that the medicament is properly deposited in the lungs. Such a device preferably should be configured to release medicament into the inspired air stream during inhalation when a defined inhalation rate has been achieved. Such a device should also ensure that medicament agglomerations and medicament carried agglomerations are broken up before reaching the patient to ensure delivery of a consistent dose of medicament to the patient. In addition, the device should enable repeated use without redosing, or redosing in a manner which is convenient and unlikely to interfere with the use of the device when the user is undergoing an asthma attack.

OBJECTS OF THE INVENTION

It is an object of the present invention to provide a medicament inhalator for the administration of dry powder medicament which controls when the medicament is made available for inhalation, thereby maximizing delivery of the medicament to the lungs. The medicament may be pure drug particles, or may be drug particles attached to a carrier particle, e.g. lactose.

It is another object of the present invention to provide such a medicament inhalator which is easy to use and which has either multiple dosing capabilities, or the ability to be conveniently reloaded.

It is still another object of the present invention to provide such a medicament inhalator which is mechanically simple, does not require depletable power sources and which is relatively inexpensive.

It is yet another object of the present invention to provide such a medicament inhalator which prevents the inhalation of large agglomerations or aggregations of medicament, thereby achieving improved consistency in dosing.

The above and other objects of the invention are realized in specific illustrated embodiments of a medicament inhalator having a body with a primary inhalation passage and a secondary inhalation passage disposed therethrough. The primary inhalation passage is formed by a first inhalation channel having a proximal end and a distal end, and a restricting flap or vane disposed between the distal and proximal ends. The restricting vane is rotatably disposed within the primary inhalation passage to selectively inhibit the flow of air through the first inhalation channel. Thus, as the user inhales, drawing air from the proximal end to the distal end of the first inhalation channel, the rotatable vane rotates into a position to occlude a substantial portion of the channel, thereby limiting flow through the channel.

The secondary inhalation passage is configured to receive a medicament dosing in communication therewith. The secondary inhalation passage includes a second inhalation channel, and the medicament dosing device holds a dose of medicament in fluid communication with the second inhalation channel such that air traveling through the second inhalation channel entrains the medicament for delivery to the patient.

In accordance with one aspect of the invention, the second inhalation channel preferably has a blocking member which is biased or otherwise normally disposed in a closed position. In the closed position, the blocking member prevents airflow through the second inhalation channel. The blocking member is selectively movable into an open position wherein the block member allows airflow through the second inhalation channel.

In accordance with another aspect of the invention, the blocking member is connected to the rotatable vane disposed in the first inhalation channel. When the user of the inhalator inhales, the rotatable vane rotates into a position wherein it substantially reduces or inhibits airflow through the first inhalation channel. This same action causes the blocking member to be moved into the open position and allows airflow through the second inhalation channel. As air rushes through the second inhalation channel, the medicament disposed in fluid communication with the second inhalation channel is entrained in the air and carried to the user. Thus, the medicament is provided to the user when the rate of inhalation is sufficient to ensure delivery of the medicament to the user's lungs. Thus, little medicament is wasted by being deposited along the mouth and throat of the person using the device.

In accordance with another aspect of the invention, the inhalation device provides for the administration of dry powder medicaments by temporarily diverting inspiratory flow from the first (primary) inhalation channel to the second (secondary) inhalation channel. By providing the inhalation device with a second inhalation channel which is sufficiently smaller than the primary inhalation channel and which is nonlinear, airflow through the secondary inhalation channel is relatively vigorous and turbulent when the blocking member is moved out of the blocking position. The vigorous airflow helps to entrain the medicament, while promoting deagglomeration of the medicament particles, deagglomeration of the medicament/carrier particles and facilitating drug particle removal from the carrier particles. Additionally, the nonlinear second inhalation channel may be formed with a portion specifically configured to form an impact surface(s). As the particles of medicament are forcefully drawn through the second inhalation channel, they collide with the impact surface, thereby breaking up any agglomeration of the medicament particles, any agglomeration of the medicament/carrier particles, and facilitating drug particle removal from the carrier particles.

In the alternative to the above, a deaggregation channel may be disposed along the primary inhalation passage to break up aggregations of medicament which are entrained by the airflow. The deaggregation channel may utilize sharp turns in direction or a zig-zag like flow pattern to cause aggregations to be impacted against side walls and thereby ensure that particle size is kept reasonably small.

In accordance with another aspect of the present invention, the medicament inhalator may be configured for use with a medicament disk having a plurality of blisters containing the medicament thereon. At or before the beginning of inhalation, the user presses a lancing mechanism to puncture a blister containing medicament. Preferably, the medicament disk is positioned along the secondary inhalation passage such that at least some of the air drawn through the secondary inhalation passage passes through the blister, and thereby ensures that nearly all of the medicament is carried to the user.

In accordance with yet another aspect of the present invention, the medicament inhalator may be configured to receive a windable tape. The windable tape is provided with a plurality of dosing units, typically in the form of small blisters filled with medicament along the tape. With each use of the medicament inhalator, the tape is drawn through the inhalator. Once all of the dosing units on the tape have been consumed, the tape is replaced.

In accordance with still another aspect of the present invention, the medicament is provided by a replaceable dosing cartridge which contains bulk powdered medicament in a reservoir. Before or during each use, the dosing cartridge is accessed in such a manner as to provide a desired dose of medicament. The dose is disposed in fluid communication with the secondary inhalation passage so that the medicament will be entrained in air flowing therethrough and be carried to the lungs of the user.

In accordance with still yet another aspect of the present invention, the medication can be disposed in a single medicament container and can be loaded before each use. The loading receptacle may be specifically designed to hold the container for use whenever needed. In such a configuration, the receptacle is easily reached to facilitate rapid replacement of the medicament container is necessary.

In accordance with a preferred embodiment of the invention, the secondary inhalation passage feeds into a distal portion of the primary inhalation channel, i.e. distally from the rotatable vane, or into a common channel. Thus, the user places his or her mouth at the distal end of the primary inhalation channel and inhales. Initially, airflow is exclusively through the primary inhalation channel. However, as the rotatable vane rotates into a blocking or inhibiting position, it significantly interferes with airflow from the proximal end to the distal end of the primary inhalation channel. At the same time, movement of the rotatable vane moves the blocking member, thereby allowing airflow through the secondary inhalation passage—dispensing medicament into the distal portion of the primary inhalation channel or a common channel. During such, the user is obtaining a significant portion of the air inhaled through the secondary inhalation passage. This air carries the medicament to the patient's lungs. The rotatable vane may either continue to rotate, ultimately rotating into a position wherein it no longer provides a significant impediment to flow through the primary inhalation channel, or the rotatable vane may be held in a position in which it restricts inspiratory air flow until inhalation is completed. When the rotatable vane continues to obstruct airflow through the primary inhalation passage, the user is forced to inhale more slowly and deposition of the medicament in the deep lung is maximized.

Once inhalation is completed, the rotatable vane returns to its original position. Likewise, the blocking member returns to its biased or closed position where it blocks airflow through the secondary inhalation passage.

Also in accordance with a presently preferred embodiment, the impact surfaces may either be disposed in the secondary inhalation passage, or in the distal portion of the primary inhalation passage or common passage at a location which is distal to the point at which the secondary inhalation passage feeds into the primary inhalation passage. Thus, the impact surfaces may be formed as nonlinear walls along the distal portion of the primary inhalation passage which are configured for contacting by the medicament particles after they have reached full velocity while entrained in the air flow. In such a position, the impact surfaces ensure that any large agglomerations are broken up prior to leaving the device.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1:
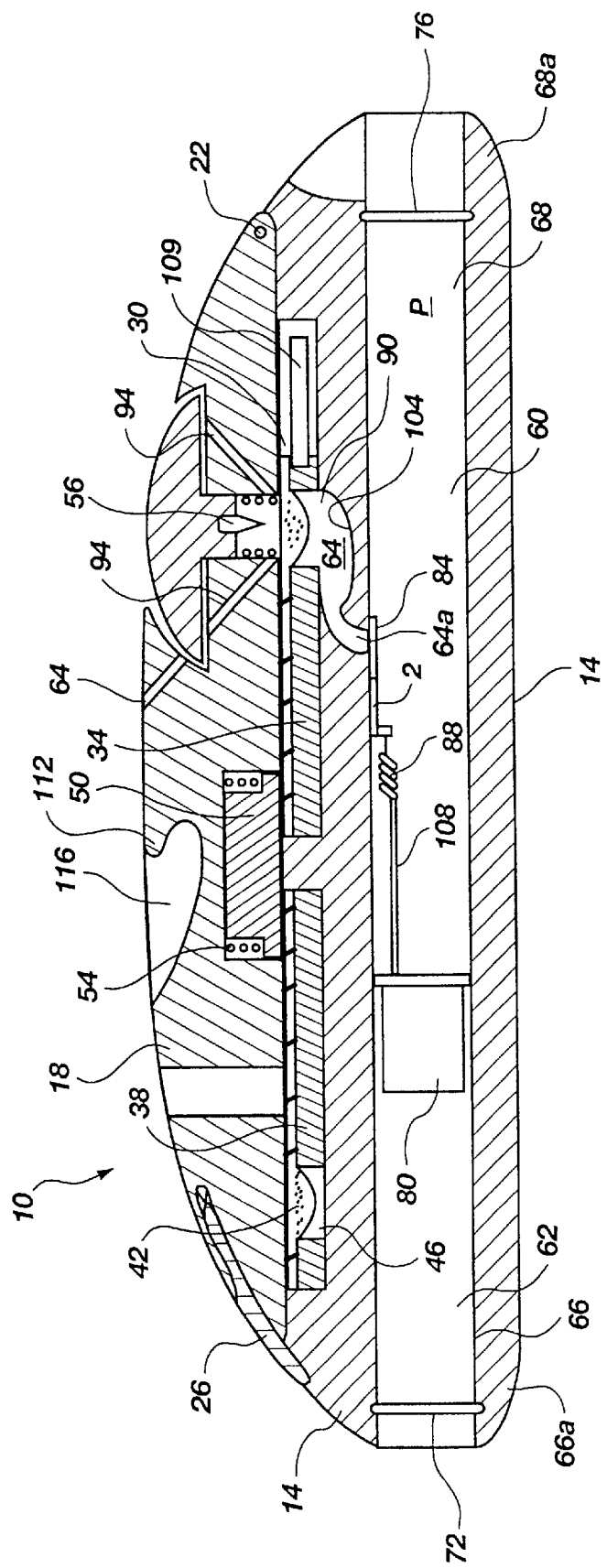
FIG. 1 shows a side cross-sectional view of the medicament inhalator showing the primary and secondary inhalation passages, a medicament dosing disk, a rotatable vane and a blocking member all disposed within the body of the inhalator.
Figure 1A:
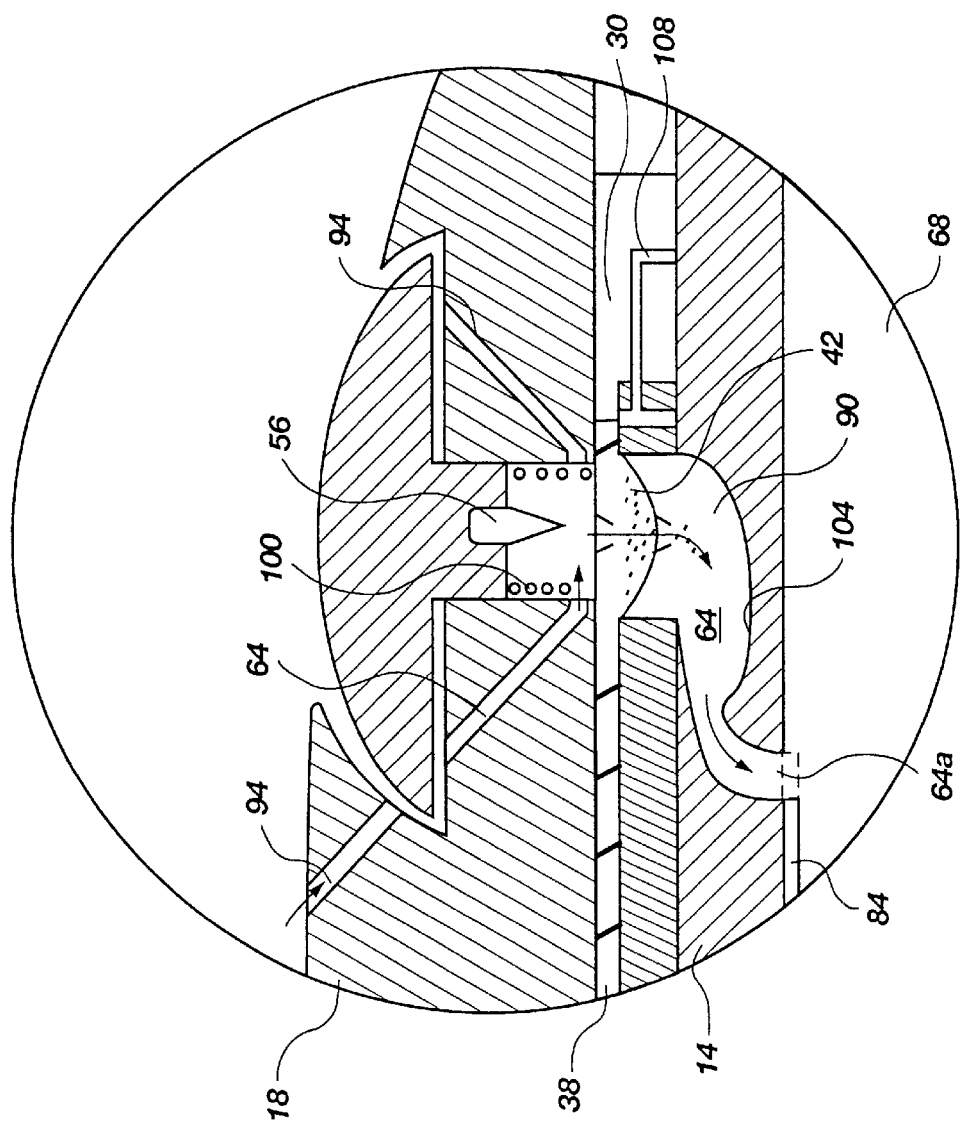
FIG. 1A shows a close-up view of the second inhalation channel and the blocking member.
Figure 1B:
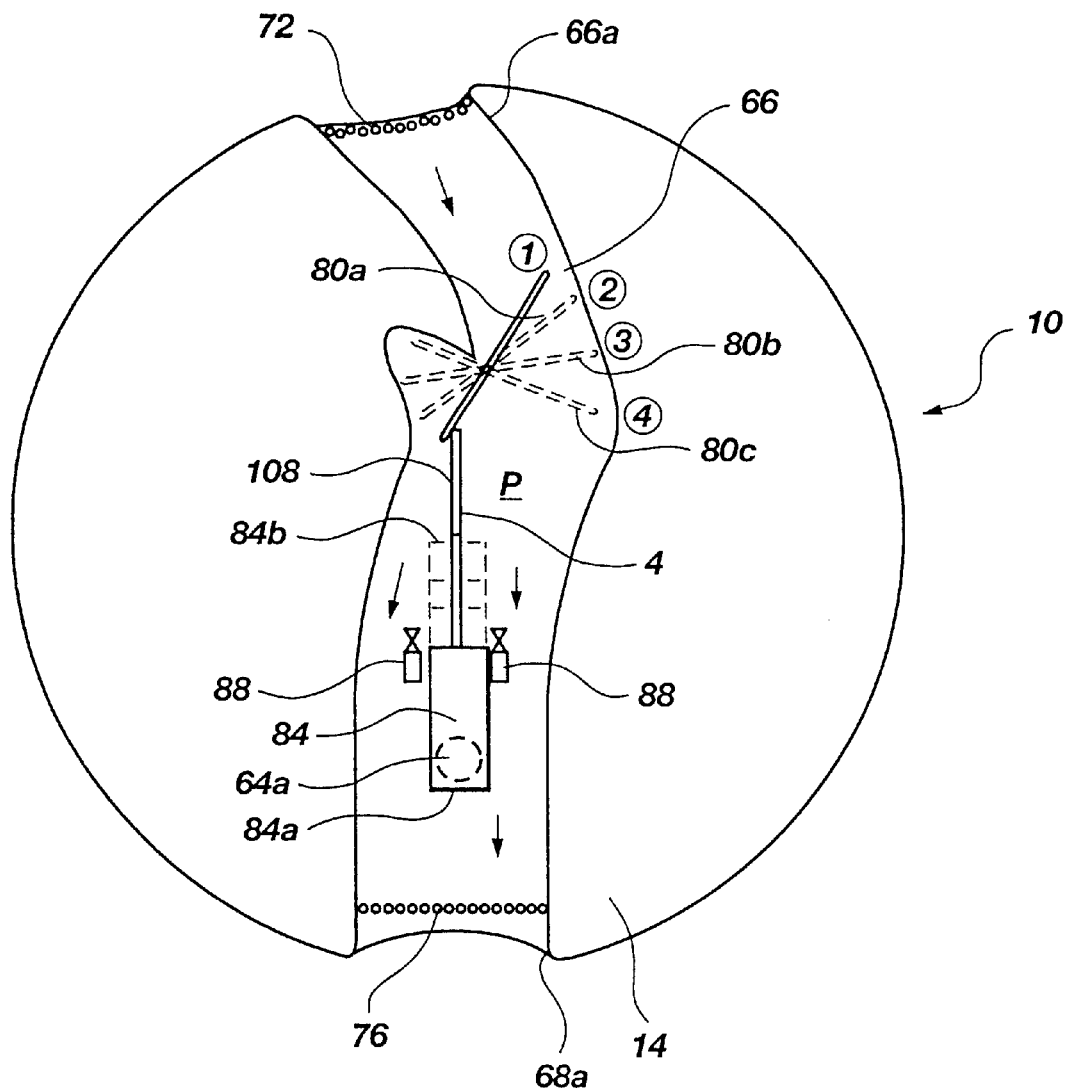
FIG. 1B shows a horizontal cross-sectional view of the inhalator of FIGS. 1 and 1A taken through the primary inhalation passage and looking upwardly.

Referring to FIGS. 1, 1A and 1B, there is shown a side cross-sectional view of a medicament inhalator, generally indicated at 10, for selectively releasing medicament while a user thereof inhales. The medicament inhalator 10 includes a housing with a body 14 and a cover 18. The cover 18, in the embodiment shown in FIG. 1, is attached to the body 14 by a hinge 22. A sliding retention clip 26 is disposed opposite the hinge 22 and disposed to engage the cover 18 to selectively maintain the cover in place.

Disposed between the body 14 and the cover 18 is a cartridge receiving cavity 30 which is configured to receive a cartridge containing medicament. The cartridge receiving cavity 30 has a cartridge receiving plate 34 which is used to support a medicament cartridge 38. Because the medicament cartridge 38 of FIG. 1 is a disk having a plurality of medicament-filled blisters 42, the cartridge receiving plate 34 has an annular channel 46 formed therein in alignment with the blisters of the disk. If desired, the medicament cartridge 38 can also be held in place by a piston 50 which nests in the cover 18, and which is biased toward the body 14 by a spring 54.

The cover 18 also includes a spring loaded lancet 56 which is disposed adjacent the cartridge receiving cavity 30. The lancet 56 is positioned so that, when pressed by the user, the lancet punctures one of the medicament-filled blisters 42 on the medicament cartridge. As will be discussed in detail below, the medicament-filled blister 42 which is penetrated by the lancet 56 is disposed in communication with an inhalation passage which enables the medicament released from the blister to be carried into the lungs of the user.

The medicament inhalator 10 includes a primary inhalation passage 60 which extends through the body 14, and a secondary inhalation passage 64 which extends through the cover 18 and part of the body 14. The secondary inhalation passage 64 terminates in an opening 64a into the primary inhalation passage 60. The various aspects of the secondary inhalation passage 64 will be discussed momentarily.

The primary inhalation passage 60 is formed by an elongate first inhalation channel 62 which extends through the length of the body 14. The first inhalation channel 62 has a proximal portion 66 with a proximal end 66a and a distal portion 68 with a distal end 68a. A screen 72 is disposed at the proximal end 66a and another screen 76 is disposed at the distal end 68a to prevent accidental aspiration of foreign particles.

Disposed between the proximal portion 66 and the distal portion 68 of the primary inhalation channel 60 is a rotatable vane 80. The rotatable vane 80 is disposed so that it may pivot between a first position, indicated at 80a (FIG. 1B), wherein the rotatable vane provides minimal interference to airflow from the proximal end 66a to the distal end 68a of the first inhalation channel 62, and a second position, indicated at 80b, wherein the rotatable vane provides a significant impediment to airflow from the proximal end to the distal end of the first inhalation channel. Movement of the rotatable vane 80 from the first position 80a to the second position 80b is accomplished by airflow created by the user inhaling through the distal end 68a.

The rotatable vane 80 is attached to a blocking plate 84 which is disposed in the first inhalation channel 62 at the opening 64a where the secondary inhalation passage 64 enters into the primary inhalation passage 60. The blocking plate 84 is biased by a spring 88 into a first, closed position (shown in FIG. 1) wherein the blocking plate 84 prevents air from the secondary inhalation passage 64 from flowing into the primary inhalation passage 60. The rotation of the rotatable vane 80 into the second position 80b moves the blocking plate 84 into a second, open position as shown in FIG. 1A. When the blocking plate 84 is in the second, open position, the secondary inhalation passage 64 is disposed in fluid communication with the primary inhalation passage.

When the rotatable vane 80 is disposed in the second position 80b, airflow through the primary inhalation passage 60 is restricted. While airflow through the secondary inhalation passage 64 will attempt to compensate for the deficiency, the smaller diameter of the secondary inhalation passage will limit its ability to provide a large quantity of air. Thus, the airflow rate through the inhalator 10 is slowed, causing the patient to exert a slow and prolonged effort to inhale. This effort, in turn, maximizes medicament penetration into the deep lung.

Referring specifically to FIG. 1A, there is shown a close-up of the secondary inhalation passage 64 and the structures adjacent thereto. The secondary inhalation passage 64 is formed from a second inhalation channel 90 which extends from the cartridge receiving cavity 30, through part of the body 14, and into the first inhalation channel 62, and at least one third inhalation channel 94 which extends through the cover 18 and into the cartridge receiving cavity 30.

To use the inhalator, the user presses the lancet 56 downward to puncture the medicament-filled blister 42. A spring 100 is disposed below the lancet 56 to return it to its original position. The user then inhales through the primary inhalation passage 60. As the rotatable vane 80 rotates in the first inhalation channel 62 to occlude airflow from the proximal end 66a to the distal end 68a, the rotatable vane 80 slides the blocking plate 84 into the second, open position. Because of the restriction on airflow created by the rotatable vane 80, a vacuum is created in the distal portion 68 of the primary inhalation channel. The movement of the blocking plate 84 into the second, open position enables air to rush through the secondary inhalation passage 64. The air enters the third inhalation channels 94, flows through the punctured medicament-filled blister 42 and then through the second inhalation channel 90. Because of the vigorous airflow which is produced due to the vacuum in the first inhalation channel 62, the medicament is forced out of the medicament-filled blister 42 and into forceful impact with an impaction surface(s) 104. The impaction surface(s) 104 breaks up any agglomeration in the medicament particles, any agglomeration of the medicament/carrier particles and facilitates drug removal from the carrier particles. This enables the medicament to be carried deeper into the lungs.

After impacting the impaction surface(s) 104, the medicament is carried by the airflow through the opening 64a and into the distal portion of the first inhalation channel 62. The medicament is then carried out through the screen 76 (FIG. 1) and into the user's lungs. Because flow through the secondary inhalation passage 64 is not enabled until the rotatable vane 80 rotates into a second position, the user achieves a desired inhalation flow rate before the medicament is supplied to the user.

Prior to the next use of the medicament inhalator 10, a sliding index advance 109 or some other advancement mechanism is used to rotate the medicament cartridge 38. Rotation of the medicament cartridge 38 places an unused medicament-filled blister 42 beneath the lancet 56 and along the secondary inhalation passage 64.

Once each of the medicament-filled blisters 42 has been used, the cartridge 38 must be replaced. This is accomplished by sliding the retention clip 26, while pulling upwardly on a finger hold 112 formed by a depression 116 in the cover 18. The used disk 38 is removed, and a new disk is inserted into the cavity 30. The cover 18 is then closed and the medicament inhalator is again ready for use.

Referring now to FIG. 1B, there is shown a horizontal cross-sectional view of the medicament inhalator 10 taken through the primary inhalation passage 60 looking upwardly. As shown in FIG. 1B, the rotatable vane 80 is disposed in the first position, indicated at 80a. The blocking plate 84 is disposed in a first, closed position 84a. As the user places the distal end 68a of the body 14 to his or her lips and inhales, the rotatable vane 84 rotates from the first position 84a to the second position 84b, thereby inhibiting airflow from the proximal end 66a to the distal end 68a. The rotation of the rotatable vane 80 moves the blocking plate 84 via a linkage 108, and exposes the opening 64a of the secondary inhalation passage 64. Thus, as the rotatable vane 80 inhibits airflow from the proximal end 66a to the distal end 68a of the first inhalation channel 62, the second inhalation channel 90 is disposed in communication with the distal portion 68 of the first inhalation channel, thereby providing air and medicament for inhalation by the user.

Once the user stops inhaling, the rotatable vane 80 is returned by the spring 88 and linkage 108 to its original position 80a. The spring 88 also moves the blocking plate 84 back into its first, closed position, thereby preventing airflow through the secondary inhalation passage.

By use of the spring's 88 resistance to movement of the rotatable vane 80 and blocking plate 84, the embodiment of the present invention shown in FIGS. 1 through 1B is designed to ensure that the user achieves a desired airflow rate before the medicament is released into the user's lungs. For example, a user will initially inhale at a first rate. The rotation of the rotatable vane 80, however decreases the rate at which the user can inhale to a second, slower rate. Due to the second, slower rate, most of the medicament is insured of reaching deep within the user's lungs, rather than simply being deposited in the mouth or throat of the user. Control over the airflow rate achieved prior to release of the medicament can be achieved by controlling the tension of the spring. Thus, for example, a children's version of the device may use a spring having lower tension than a version configured for adults. The exact tension desired will be easily determinable by those skilled in the art.

Figure 2A:
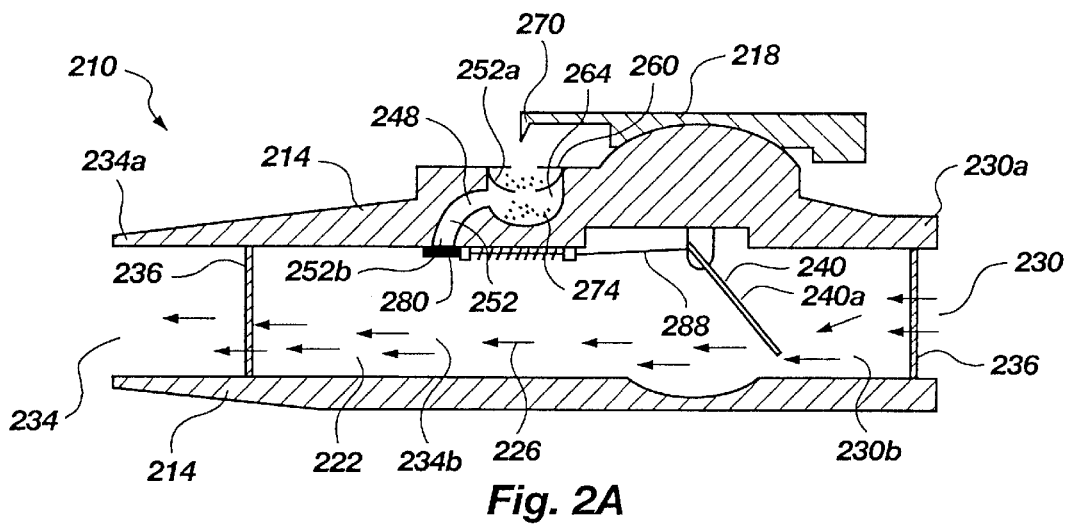
FIG. 2A shows a side cross-sectional view of another embodiment of an inhalator made in accordance with the principles of the present invention, as the embodiment is configured at the beginning of inhalation.

Turning now to FIG. 2A, there is shown a side cross-sectional view of an alternate embodiment of a medicament inhalator, generally indicated at 210, made in accordance with the principles of the present invention. Unlike the embodiment of FIGS. 1 through 1B, the medicament inhalator 210 includes a one-piece housing or body 214 with a lancet 218 pivotably or slidably attached thereto.

A primary inhalation passage 222 is formed in the body 214 of the medicament inhalator 210 by an elongate first inhalation channel 226 which extends from an opening 230 at a proximal end 230a of the body to an opening 234 at a distal end 234a of the body. Screens 236 are disposed adjacent each end to prevent accidental aspiration of foreign particles. The elongate first inhalation channel 226 is divided into a proximal portion 230b and a distal portion 234b by a rotatable vane 240.

The body 214 also includes a secondary inhalation passage 248 which is formed by a second inhalation channel 252 extending from a first opening 252a in the exterior of the body 214, to a second opening 252b into the distal portion 234b of the first inhalation channel 226. The first opening 252a of the second channel 252 is configured for receiving a medicament holding device, such as an elongate tape 260, with a plurality of medicament-filled blisters 264 disposed thereon. The elongate tape 260 is preferentially positioned so that downward pivoting movement of the lancet 218 causes a sharp projection 270 disposed thereon to penetrate through the medicament-filled blister 264 disposed in the first opening 252a of the second inhalation channel 252. As is shown in FIG. 2A, such a puncture enables some of the medicament to fall from the medicament-filled blister 264 to an impact surface 274 disposed along the second inhalation channel 252.

Airflow between the first inhalation channel 226 and the second inhalation channel 252 is selectively prevented by a blocking plate 280 which is biased in a first, closed position wherein the blocking plate covers the second opening 252b in the second inhalation channel. Because any significant airflow through the punctured blister 264 or the secondary inhalation channel 252 is prevented while the blocking plate 280 covers the second opening 252b, the blocking plate 280 must be moved for the medicament to be carried to the user.

To use the medicament inhalator 210, the user places the distal end 234a to his or her mouth and inhales through the opening 234. Initially, the airflow toward the distal end 234a of the elongate first inhalation channel 226 comes exclusively from the proximal end 230a. However, the airflow begins to rotate the rotatable vane 240 out of its original position 240a (FIG. 2A) and into an intermediate, restricting position 240b (FIG. 2B) wherein the rotatable vane 240 obstructs airflow through the elongate first inhalation channel 226. The rotatable vane 240 is connected to the blocking plate 280 via a linkage 288. As the rotatable vane 240 moves into the intermediate position 240b, the linkage 288 moves the blocking plate 280 into a second, open position, wherein the blocking plate no longer covers the opening 252b at the end of the secondary inhalation passage 248. Thus, as air flows through the elongate first inhalation channel 226, the second inhalation channel 252 is opened. Airflow through the second inhalation channel 252 is turbulent and is designed to promote deaggregation of medicament particles, deaggregation of medicament/carrier particles, and to maximize removal of drug particles from the carrier particles. The airflow is drawn through the medicament-filled blister 264 and entrains the medicament. Any large agglomeration of medicament/carrier particles is caused to forcefully impact against at least one impact surface 274 and is thereby broken into smaller pieces.

Continued inhalation moves the rotatable vane 240 into a final position 240c (FIG. 2C), wherein the rotatable vane 240 provides minimal interference to airflow through the primary inhalation channel 226. In the final position 240c, the rotatable vane 240 also maintains the blocking plate 280 in the second, open position. Thus, as the user finishes inhalation, air is provided through both the first and second inhalation channels 226 and 252. Once the user stops inhalation, the rotatable vane 240 will return to its original position 240a (FIG. 2A) and tape 260 may be advanced to place a new medicament-filled blister 264 in the first opening 252a of the second inhalation channel 252.

Figure 2B:
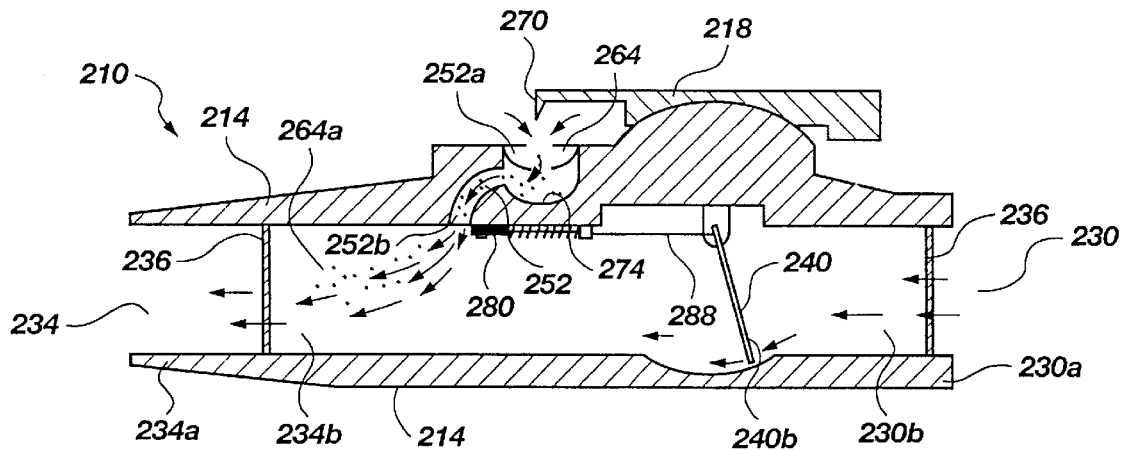
FIG. 2B shows a side cross-sectional view of the embodiment of FIG. 2A, as the medicament inhalator is configured in the middle of inhalation.
Figure 2C:
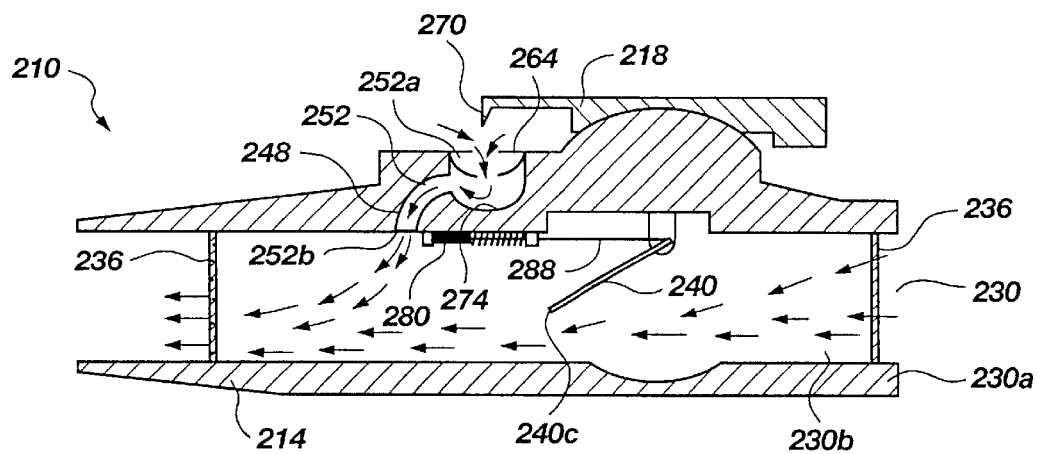
FIG. 2C shows a side cross-sectional view of the embodiment of FIGS. 2A and 2B, as the medicament inhalator is configured near the end of inhalation.

By using the configuration of the medicament inhalator 210 shown in FIGS. 2A through 2C, the medicament is provided to the user at the proper point of the inhalation profile. This ensures better delivery of the medicament to the user's lungs, and thus ensures more efficacious treatment for asthmatics and others with breathing difficulty. At the same time, the device is as simple, if not simpler, to use than the prior art and is mechanically less complex.

Figure 3A:
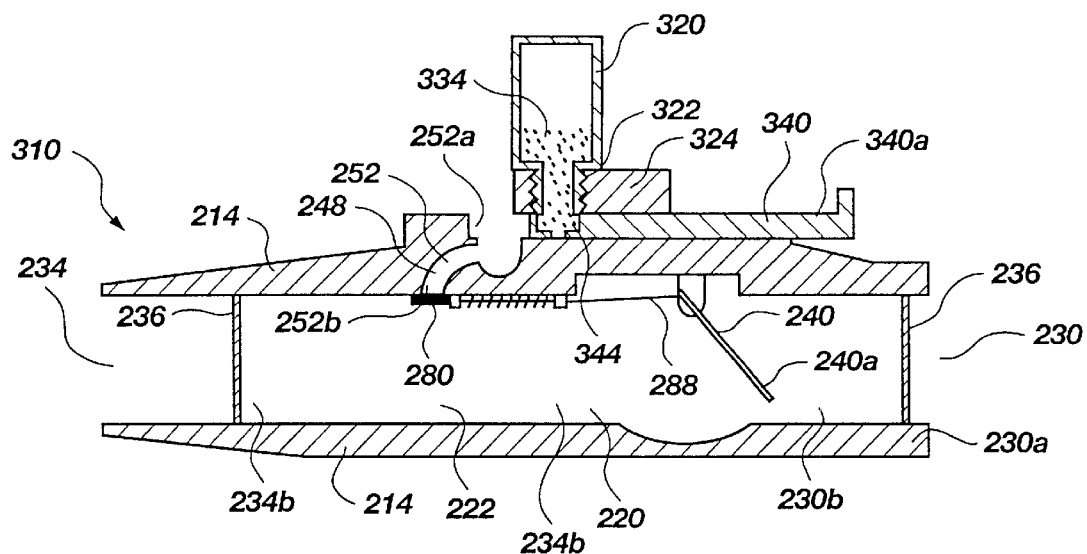
FIG. 3A shows a side cross-sectional view of another embodiment of a medicament inhalator made in accordance with the principles of the present invention, wherein the medicament dosings are provided by a dosing cartridge having a reservoir with bulk medicament disposed therein, and a dosing plunger disposed in a refill position.
Figure 3B:
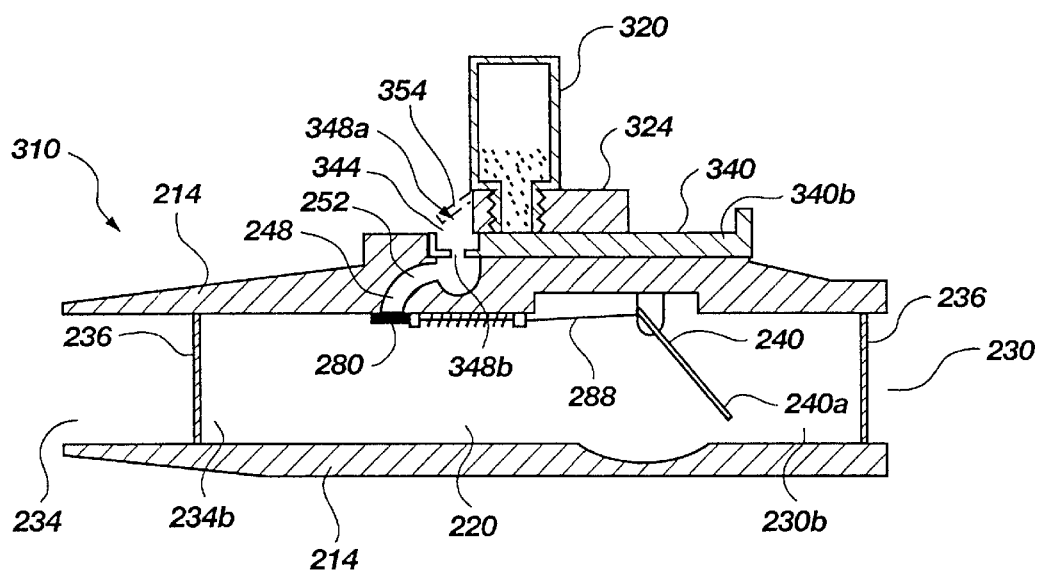
FIG. 3B show a side cross-sectional view of the medicament inhalator of FIG. 3A, with the dosing plunger in a dosing position wherein medicament is supplied to the secondary inhalation passage.

Turning now to FIGS. 3A and 3B, there are shown side cross-sectional views of an alternate embodiment of a medicament inhalator, generally indicated at 310, made in accordance with the principles of the present invention. The medicament inhalator 310 includes a body 214, most of the portions of which are configured the same and function in the same manner as the embodiment shown in FIGS. 2A through 2C. Therefore, such portions are numbered in accordance with the numeral designations used with respect to FIGS. 2A through 2C where appropriate.

The primary difference between the embodiment shown in FIGS. 3A and 3B, compared to that shown in FIGS. 2A through 2C is the manner in which the medicament is provided to the first, upper opening 252a in the secondary inhalation channel 252. Rather than relying on a tape 260 with medicament-filled blisters 264 as discussed in FIGS. 2A through 2C, the embodiment of FIGS. 3A and 3B utilizes a bulk medicament cartridge 320 which is threadedly or otherwise engaged to a cavity 322 in a top portion 324 of the body 214.

In order to dose and distribute the medicament 334 contained within the bulk dosing cartridge 320, a dosing plunger 340 is slidably disposed in the top portion 324 of the housing. The plunger 340 has a dosing chamber 344 disposed therein. The dosing chamber 344 has an upper opening 348a which is sized to receive medicament 334 from the bulk medicament cartridge 320 when the plunger is disposed in a first, refill position, as indicated at 340a in FIG. 3A.

The dosing chamber 344 also has a lower opening 348b disposed opposite the upper opening 348a. When the dosing plunger 340 is in the first, refill position 340a, the lower opening 348b is essentially closed by the body 214. However, once the plunger is moved into a second, dosing position, indicated in FIG. 3B at 340b, the lower opening 348b is disposed along the second inhalation channel 252. When airflow through the second inhalation channel 252 is established, air passes through the upper opening 248a, through the dosing chamber 344 and through the lower opening 348b, thereby entraining the medicament carried in the dosing chamber and carrying it to the user. As shown in FIG. 3B, a screen or shield 354 may also be provided to prevent airborne materials from being sucked into the dosing chamber 344 or secondary inhalation channel during inhalation.

In use, the medicament inhalator 310 shown in FIGS. 3A and 3B operates in substantially the same manner as the medicament inhalator 210 shown in FIGS. 2A through 2C, with the exception of the initial act making the medicament available for inhalation. With the medicament inhalator 210 of FIGS. 2A through 2C, the user initially places the tape 260 in the opening 252a in the secondary inhalation channel 252 and then presses on the lancet 218 so that the sharp projection 270 punctures the medicament-filled blister 268. With the medicament inhalator 310 of FIGS. 3A and 3B, the dosing plunger 340 is moved into the first, refill position 340a to allow medicament 334 from the bulk medicament cartridge 320 to fill the dosing chamber 344. The plunger 340 is then advanced into the dosing position 340b, wherein the dosing chamber 344 is disposed in fluid communication with the secondary inhalation passage.

The user breathes in the same manner with either medicament inhalator, and the rotatable vane 240 moves from the initial position 240a (FIGS. 2A, 3A and 3B) into the intermediate position 240b (FIG. 2B) and into the final position 240c (FIG. 2C). The movement of the rotatable vane 240 moves the blocking plate 280, thereby placing the second inhalation channel 252 in communication with the distal portion 234b of the first inhalation channel 226, thereby supplying medicament to the user.

While numerous devices could be provided to determine when the bulk medicament cartridge 320 is empty, the simplest mechanism for ensuring that medicament is present is to provide a bulk medicament cartridge which is transparent. Once the user can no longer see the medicament in the bulk medicament cartridge 320, the cartridge can be unscrewed from the top 324 and replaced with a new cartridge. Of course, those skilled in the art will appreciate that the medicament inhalator 310 could be easily adapted for use with other types of bulk medicament cartridges.

In addition to the benefits discussed above, the present invention overcomes another common cause of agglomeration of medicament and/or carrier particles. A user will often place an inhalator to his or her lips slightly before the act of inhaling has begun. Often, this results in the inhalator being disposed in front of the user's mouth shortly before the completion of exhalation. Some of the warm, moist air from the user's mouth is thus channeled into the inhalator. This warm, moist air tends to promote agglomeration of the medicament particles and/or the carrier particles.

The present invention, however, avoids this problem. The blocking plate 84 (FIGS. 1–1C) or 280 (FIGS. 2A–3B) maintains the medicament in position where it is isolated from the user's breath. Thus, even if the user were to completely exhale through the primary inhalation passage 60 (FIGS. 1–1C) or 220 (FIGS. 2A–3B), the exhaled air would not come in contact with the medicament and would not cause agglomeration.

Figure 4:
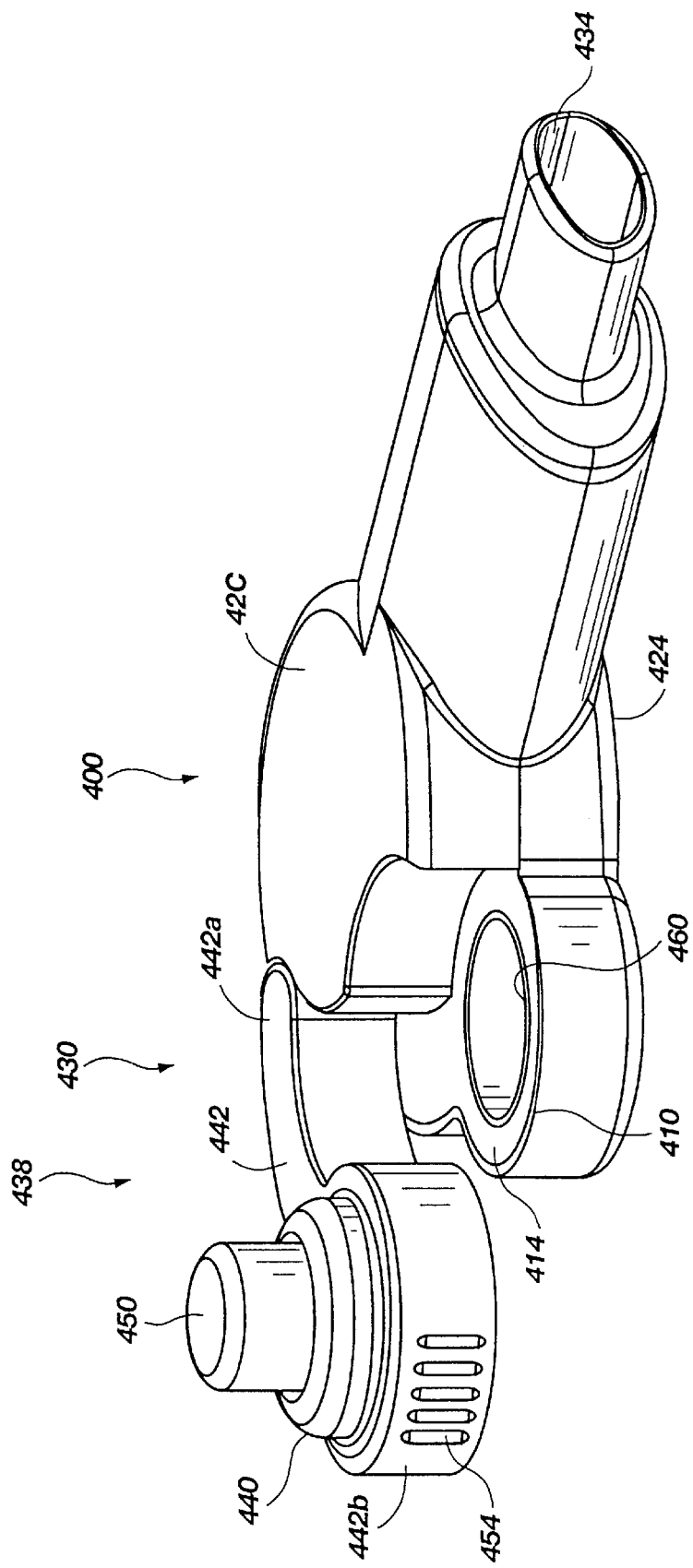
FIG. 4 shows a perspective view of another embodiment of a medicament inhalator of the present invention wherein a single dose blister pack is used to provide medicament, the medicament inhalator being in a reloading orientation.
Figure 4A:
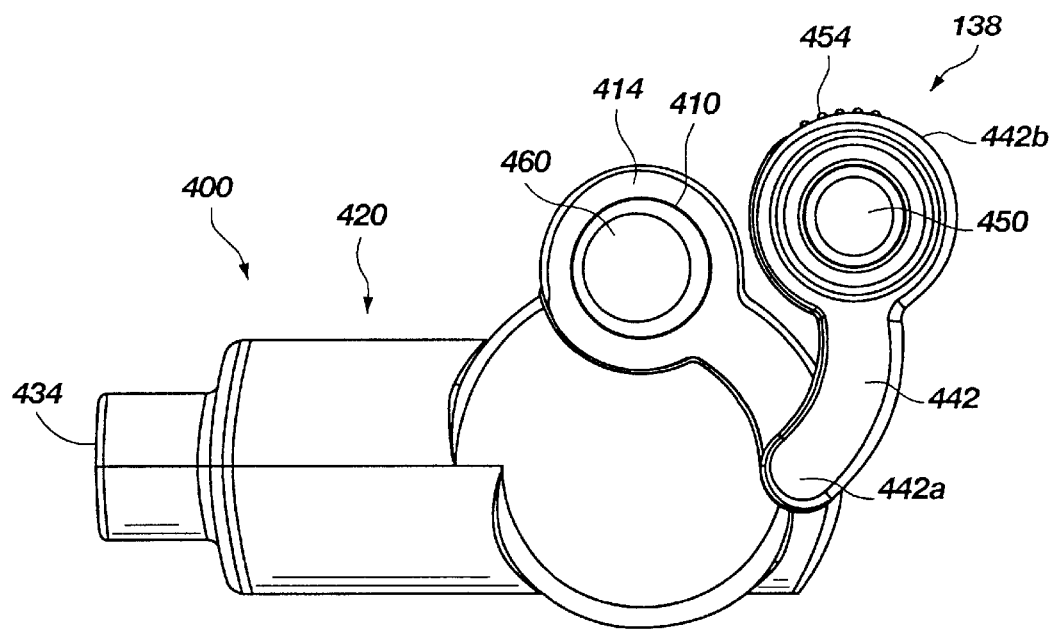
FIG. 4A shows a top view of the medicament inhalator of FIG. 4 in the reloading orientation.
Figure 4B:
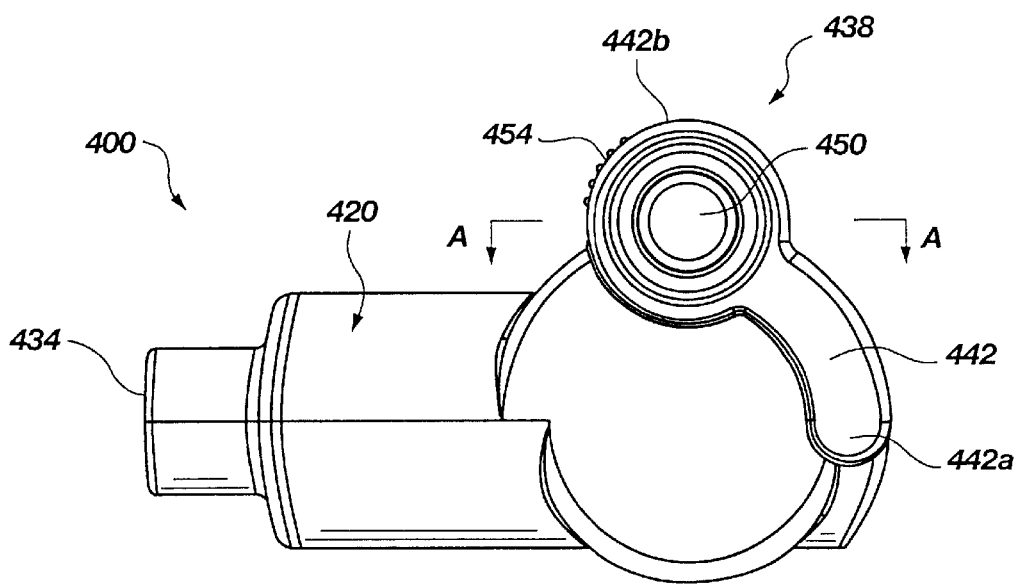
FIG. 4B shows a top view of the medicament inhalator of FIG. 4 in a loaded orientation.
Figure 4C:
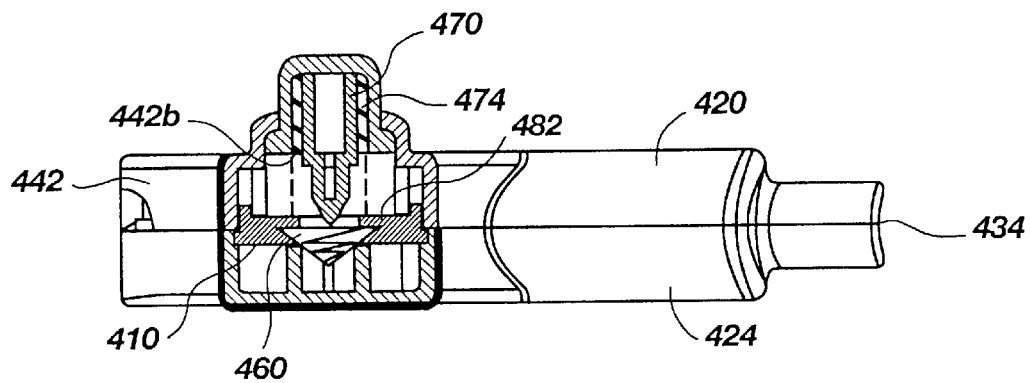
FIG. 4C shows a cross-sectional view of the lancet mechanism of FIG. 4B taken through the plunger button and the second end of the plunger arm.
Figure 4D:
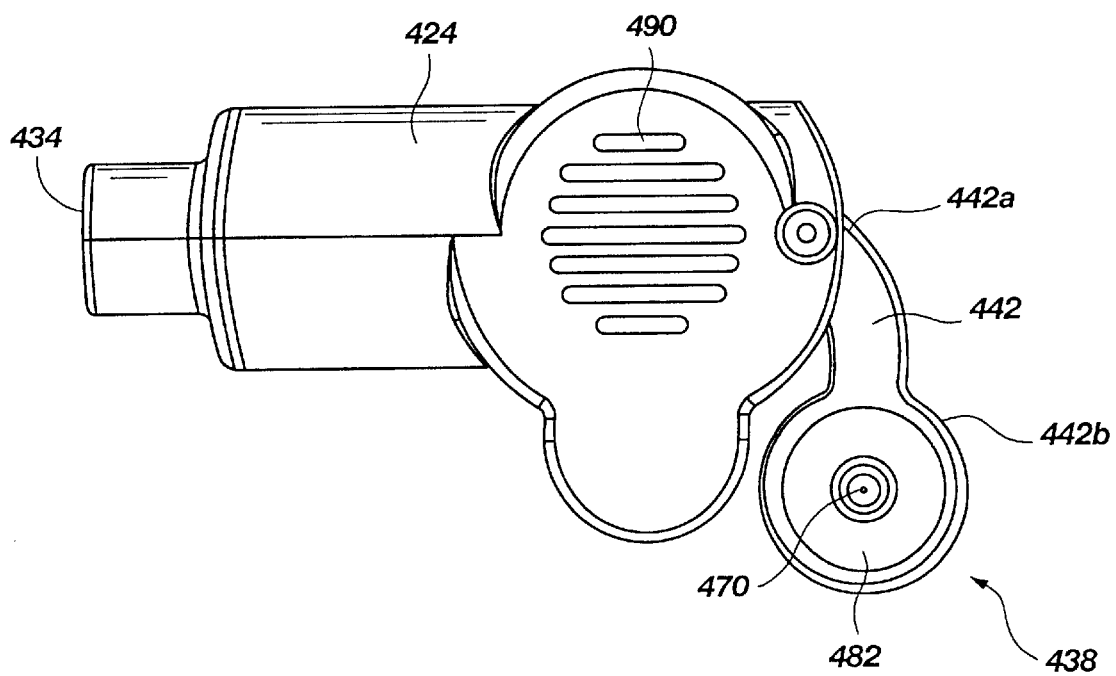
FIG. 4D shows a bottom view of the medicament inhalator shown in FIGS. 4 through 4C.
Figure 4E:
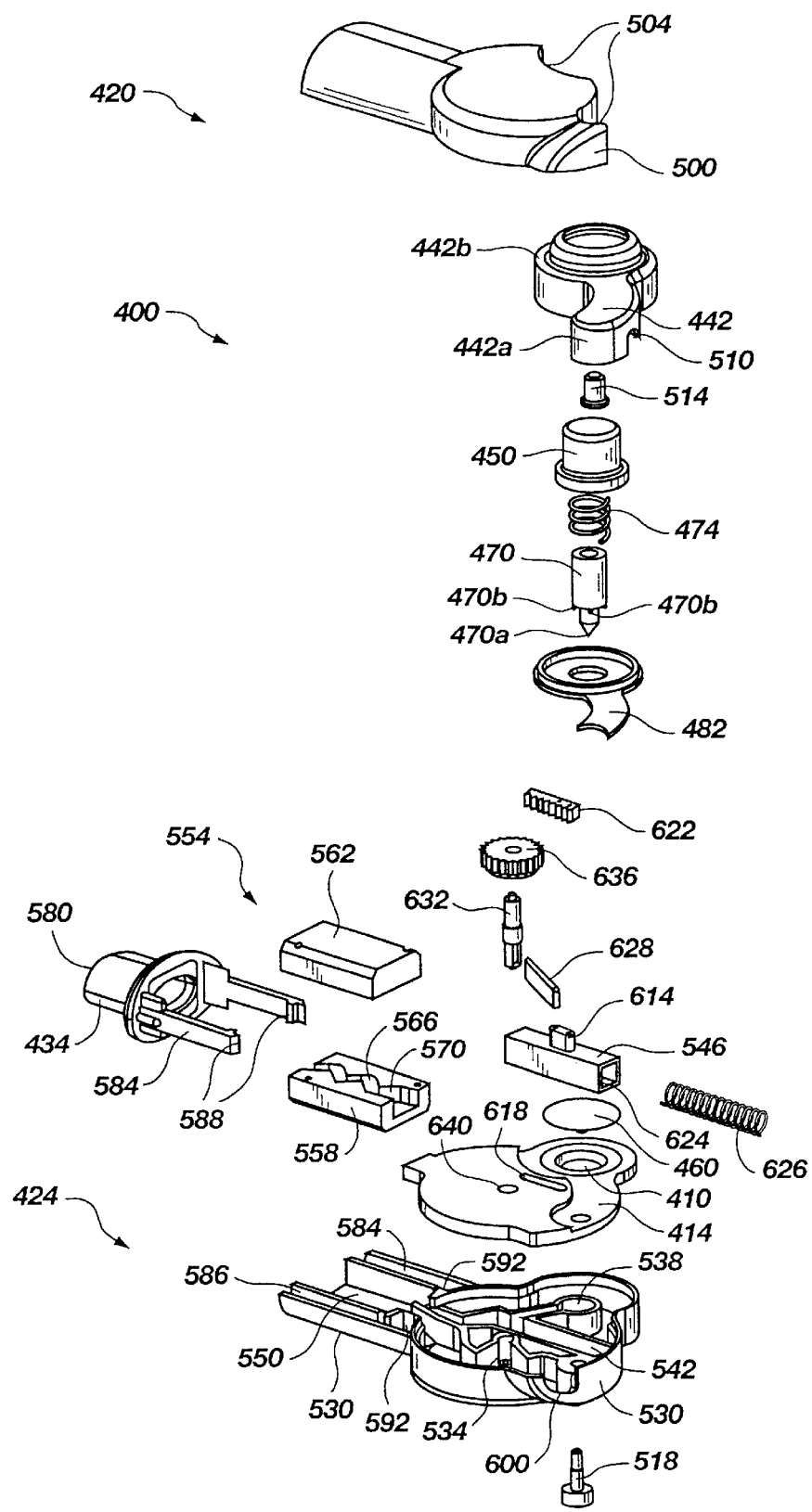
FIG. 4E shows an exploded view of the medicament inhalator of FIGS. 4 through 4D.
Figure 4F:
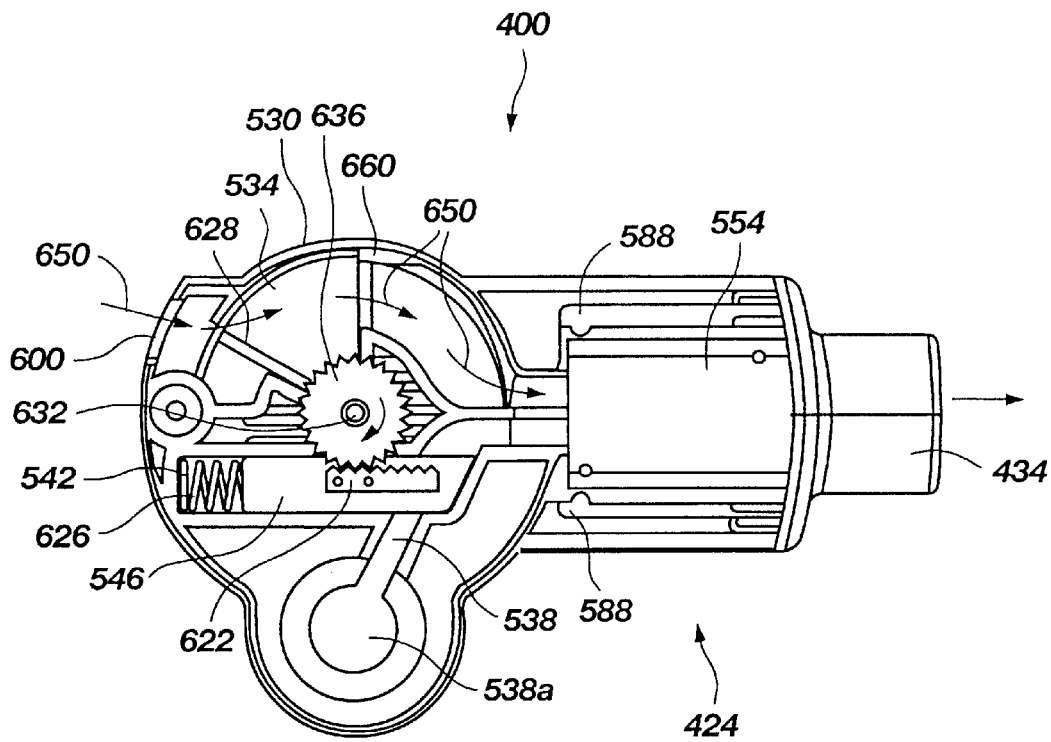
FIG. 4F shows a plan view of the bottom portion of the medicament inhalator of FIGS. 4 through 4E, including the inhalation passages, wherein the blocking member is biased in a closed position.

Turning now to FIGS. 4 through 4F, there is shown yet another embodiment incorporating the aspects of the present invention. Referring specifically to FIG. 4, there is shown a close-up, perspective view of a medicament inhalator, generally indicated at 400, made in accordance with the principles of the present invention. As will be explained in additional detail, the medicament inhalator 400 utilizes a single dose blister pack to provide medicament for inhalation. The medicament inhalator 400 in FIG. 4 is in a reloading position, wherein a blister pack of medicament 460 is disposed on a receptacle, generally indicated at 410, formed in a separator plate 414 which will be discussed in detail.

The medicament inhalator 400 includes an upper portion 420 and a lower portion 424. The upper portion 420 includes an actuator mechanism, generally indicated at 430, and also forms a portion of a mouthpiece 434 through which a user inhales to receive medicament in accordance with the teachings of the present invention.

The actuator mechanism 430 mechanism includes a lancing mechanism, generally indicated at 438. The lancing mechanism 438 of the embodiment shown in FIG. 4 includes a button plunger assembly 440 which allows loading of the blister pack onto the receptacle 410 formed in the separator plate 414, and lances the blister pack when the user needs medication.

The plunger assembly 440 includes a plunger arm 442 which is pivotably connected at a first end 442a to either the remainder of the top portion 420 or, more preferably, to the bottom portion 424. Pivoting of the first end 442a of the plunger arm 442 typically allows for a range of movement of about 45 degrees. Such a range of movement is sufficient to enable replacement of a blister pack disposed on the receptacle 410 of the separator plate 414, while requiring minimal movement of the plunger arm into a position (not show in FIG. 4) wherein the lancing mechanism 438 can pierce the blister pack and deliver medicament to the user. Also present in the first end 442a of the plunger arm 442, although not visible in FIG. 4, is a vent to allow air flow through the plunger arm, the blister pack, and ultimately through the lower portion 424 of the medicament inhalator 400.

A second end 442b of the plunger arm 442 opposite the first end 442a includes a plunger button 450 which is part of the lancing assembly 440. Disposed within the plunger button 450 and discussed in detail below is a biased lancet which is configured to pierce the blister pack 46 when the user of the medicament inhalator 400 is ready for use. The second end 442a of the plunger arm 442 also includes a plurality of ridges 454 which are configured to facilitate movement of the plunger arm between the reload position shown in FIG. 4 and the loaded position shown in FIG. 4B. Typically movement of the plunger arm 442 will be accomplished with a finger or thumb of the user, and the ridges 454 provide traction for the same.

Turning now to FIG. 4A, there is shown a top view of the medicament inhalator 400 shown in FIG. 4 in the reloading position, wherein the plunger arm 442 is rotated away from the remainder of the top portion at an angle of about 45 degrees. This position allows a used blister pack to be removed from the receptacle and a new blister pack 460 to be disposed in the receptacle 410 of the separator plate 414. Once the new, medicament containing blister pack 460 is disposed in the receptacle 410, the plunger arm 442 is rotated about its first end 442a so that the second end 442b of the plunger arm is disposed above the receptacle as shown in FIG. 4B. In such a loaded orientation, the lancing mechanism 438 is able to pierce the blister pack 460 when the user presses downwardly on the plunger button 450.

FIG. 4C shows a cross-sectional view taken through the second end 442b of the plunger arm 442 along plane A—A in FIG. 4B. The cross-sectional view shows in more detail the lancing mechanism 438 which is used to pierce the medicament containing blister pack 460 as it rests in the receptacle 410.

The lancing mechanism 438 includes the plunger button 450 which is disposed in the second end 442b of the plunger arm 442. Disposed below the plunger button 450 is a lancet 470. The lancet 470 is unique in that it provides a primary piercing element 470a which is configured with a pointed projection to pierce the blister pack 460, and a plurality of secondary piercing elements 470b which are configured with smaller, pointed projections to pierce a portion of the blister pack.

When a blister pack is pierced by a single lancet, the lancet tends to deform the upper surface of the blister pack inwardly into an inverted cone. The downwardly extending portions of the top of the blister pack interfere with the ability of airflow through the hole in the blister pack to entrain the medicament. The secondary piercing elements 470b are preferably disposed circumferentially around the primary piercing element 470a and form a plurality of small holes in the top of the blister pack 460 to ensure that adequate airflow is present to entrain the medicament contained within the blister pack.

Disposed around the lancet 470 is a spring 474. The spring 474 rests on a secondary back plate 482 so that the spring biases the plunger button 450 and the lancet 470 in an upward position. However, applying a downward force to the plunger button 450 overcomes the biasing and moves the lancet 470 downwardly so that the lancet 470 can pierce the medicament containing blister pack 460 in the receptacle 410 of the separator plate 414. Once the pressure on the plunger button 450 is released, the spring causes the lancet to resett—thus forming a self-resetting mechanism.

Once the blister pack 460 has been pierced, the vent 510 formed in the first end 442a of the plunger arm 442 allows air to flow through the plunger arm and then the blister pack. This allows medicament contained in the blister pack 460 to be entrained in the air, and eventually brought to the user.

Turning now to FIG. 4D, there is shown a bottom view of the medicament inhalator 400 with the plunger arm 442 disposed in the first, reloading position. With the plunger arm 442 swung away from the main body of the medicament inhalator 400, the lancet 470 and the secondary back plate 482 are visible.

As with the second end 442b of the plunger arm 442, the lower portion 424 of the medicament inhalator 400 may be provided with a plurality of ridges 490 which are configured to making handling the medicament inhalator more convenient. Of course, other methods for accomplishing the same purpose, such as the use of a rubber coating could also be used.

Turning now to FIG. 4E, there is shown an exploded view of the parts of the medicament inhalator 400. Beginning with the top portion 420, there is shown a top cover 500 of the medicament inhalator 400. The top cover 500 has a pair of grooves 504 formed therein to enable the first end 442a and the second end 442b of the plunger arm 442 to nest against the top cover.

As shown in FIG. 4E, a small vent 510 is formed in the first end 442a of the plunger arm 442. The vent 510 allows air to be directed through the plunger arm and then through a blister pack to entrain medicament in the air after the blister pack has been punctured by the lancet 470.

Below the plunger arm 442 is a threaded insert 514 which is disposed in the first end 442a of the plunger arm 442. The threaded insert 514 receives a shoulder screw 518 which extends through the bottom portion 424 to secure the plunger arm 442 and enable pivoting of the plunger arm between the reloading position shown in FIGS. 4 and 4A and the loaded position shown in FIG. 4B.

Also disposed in the plunger arm 442 are the plunger button 450, the lancet 470 and the spring 474 which biases the lancet 470 and the plunger button 450 in the upwardly. This keeps the lancet 470 from penetrating or otherwise interfering with the blister pack 460, except when the user desires to pierce the blister pack to release medicament.

Turning now to the lower portion 424, there is shown bottom cover 530. The bottom cover 530 includes a first inhalation passage 534 and a second inhalation passage 538. Disposed between the first inhalation passage 534 and the second inhalation passage 538 is a blocking member passage 542 which is configured to receive a blocking member 546 which is discussed in additional detail below.

The bottom cover 530 also has a cavity 550 which is configured to receive a deaggregation assembly, generally indicated at 554. The deaggregation assembly 554 includes a lower portion 558 and an upper portion 562. The lower portion 558 has a channel 566 formed therethrough. The channel 566 is nonlinear so that air passing therethrough does not follow a straight flow path. Preferably, the channel 566 has a zig-zag configuration. Such a configuration enables the walls 570 that define the channel to form impact surfaces. As medicament entrained in air passes through the channel 566, the medicament is not able to follow the curves of the channel as quickly as the air. Thus, the medicament particles impact the opposing walls 570 of the channel. The impact breaks up any aggregation of the medicament and ensures more consistent dosing of the medicament.

The upper portion 562 could be formed with a like channel, or can simply be flat so as to form an upper wall to the channel 566. Either way, the deaggregation assembly 554 improves medicament delivery.

Those skilled in the art will appreciate that the channel 566 could be viewed as a simple continuation of the channel which forms the first inhalation passage 534 with the second inhalation passage 538 terminating therein, or could be viewed as a common channel. Additionally, those skilled in the art will recognize that two separate channels could be provided. If such were done, the channel which was disposed in communication with the second inhalation passage 538 should have the impact surfaces which are formed by the zig-zag structure.

The deaggregation assembly 554 may be bonded to the lower cover 530. More preferably, however, the deaggregation assembly 554 is held in place by the mouth piece 534. While the mouth piece 434 includes an opening 580 through which the user can breath, and a pair of arms 584 which extend proximally. The arms 584 are configured to nest in a pair of grooves 586 in the bottom cover 530. Preferably, the arms 584 have barbs 588 at their proximal end for nesting in voids 592 in the bottom cover 530 to provide a snap-fit arrangement between the mouthpiece 434 and the bottom cover.

The bottom cover 530 also includes a vent 600 which is disposed in communication with the first inhalation passage 534. The vent 600 allows for air to be drawn into the first inhalation passage 534 when the user inhales through the mouthpiece 434.

Also shown in FIG. 4E is a main separator plate 414 which is configured for positioning between the bottom cover 530 and the top cover 504 and to form an upper wall of the first inhalation passage 534, the second inhalation passage 538 and the blocking member passage 542.

Disposed above the main separator plate 414 is the blocking member 546. The blocking member 546 is configured to fit in the blocking member passage 542 and to move within that passage to selectively allow or terminate airflow through the second inhalation passage 538. Thus, when assembled, the blocking member 546 is positioned below the main separator plate. The blocking member 546, however, includes post 614 which extends upwardly therefrom. The post 614 is configured for extending through a slot 618 in the main separator plate 414. The post 614 is configured for attachment to a linear gear 622 which enables movement of the blocking member 546.

The blocking member also includes a void 624 in one end. The void 624 is configured for receiving a spring 626. When the blocking member 546 is disposed in the blocking member passage 542 and the spring 626 is disposed in the void 624, the spring biases the blocking member 546 toward the distal end of the blocking member passage 542 and thereby is in a closed position preventing airflow through the second inhalation passage 538.

Also shown in FIG. 4E is a vane 628 which is configured to be positioned in the first inhalation passage 534 beneath the main separator plate 414. The vane 628 is attached to a vane shaft 632 which extends through a hole 640 formed in main separator plate 414. A vane gear 636 attaches to an opposing end of the shaft. When the vane 628 is disposed in the first inhalation passage 534 and the blocking member 546 is disposed in the blocking member passage 542, the vane gear 636 on the shaft 632 engages the linear gear 622 which is attached to the blocking member by the post 614. Thus, rotation of the vane 628 in the first inhalation passage 534 causes movement of the blocking member 546 in the blocking member passage 542.

FIG. 4E also shows the receptacle 410 in the form of an opening formed in the main separator plate 414. A blister pack 460 is disposed in the receptacle when reloading the medicament inhalator 400 for later piercing by the lancet 470.

Turning now to FIG. 4F, there is shown a plan view of the bottom cover 530 and selective pieces of the medicament inhalator 400 shown in FIG. 4E to demonstrate the working of the embodiment. The bottom cover 530 of the medicament inhalator 400 is divided into the three channels or passages. The first inhalation passage 534 extends from the vent 600 in the distal end of the bottom cover 530 to the deaggregation assembly 554 disposed adjacent the mouthpiece 438. Thus, when the user inhales through the first inhalation passage 534, the air follows the flow pattern indicated by the arrows 650.

Before inhalation occurs, the vane 628 is disposed at a proximal end of the first inhalation passage. With the vane 628 in such a position, the blocking member 546 is biased toward the distal end of the blocking member passage 542 by the spring 626. In such a position, the blocking member 542 prevents airflow through the second inhalation passage 538. Thus, if a user were to use the lancing mechanism (not shown) to pierce the blister pack, the medicament would fall into the chamber 538a at the proximal end of the second inhalation passage, but would not be delivered to the user.

When the medicament inhalator 400 is used, the user places the mouth piece 434 in his or her mouth and inhales. Initially, the airflow follows the path 650 shown in FIG. 4F. However, as the user inhales, a vacuum is created in the first inhalation channel 534. The vacuum causes the vane 628 to rotate. Eventually, the vane 628 rotates until it contacts a shelf or a stop 660 formed along the first inhalation passage 534. When the vane 628 contacts the stop 660, the vane effectively divides the first inhalation passage 534 into a proximal portion 534a and a distal portion 534b.

The vane 628 and stop 660 engagement can be configured to either prevent any airflow through the first inhalation passage 534, or, more preferably, will only cause a significant decease in the amount of airflow which can pass through the first inhalation passage. As airflow is restricted in the primary inhalation passage, resistance to inhalation is increased and the user inhales more deeply, thus expanding the lungs, resulting in greater peripheral lung deposition of drug.

Figure 4G:
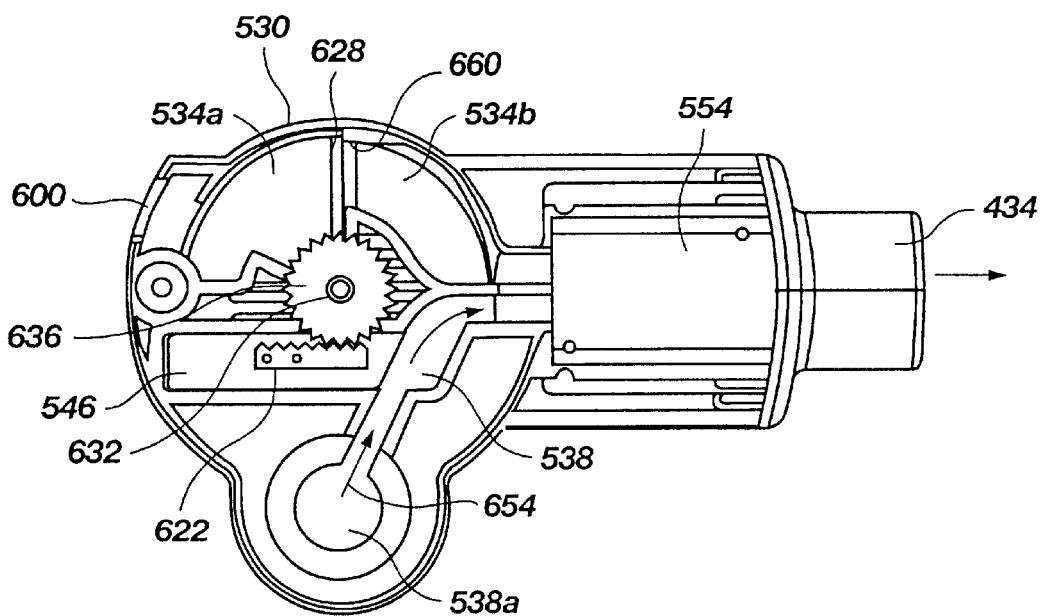
FIG. 4G shows a plan view of the bottom portion of the medicament inhalator of FIGS. 4 through 4E wherein the blocking member has been moved into the open position.

As the vane 628 rotates clockwise into the closed position shown in FIG. 4G, the vane gear 636 which is attached to the vane by the vane shaft 632 also rotates in a clockwise rotation. As the vane gear 636 rotates clockwise, it causes the linear gear 622 to be moved proximally. Because the linear gear 622 is attached to the blocking member 546, proximal movement of the linear gear also causes proximal movement of the blocking member, overcoming the biasing of the spring 626.

As the blocking member 546 moves proximally in the blocking member passage 542, the second inhalation passage 538 is opened to allow flow as indicated by arrows 654. Thus, as the airflow through the first inhalation passage 534 is inhibited, airflow through the second inhalation passage is allowed. Any medicament in the chamber 538*a* or in the blister pack (not shown) will be carried passed the blocking passage and will join with any airflow from the first inhalation passage 534 in the deaggregation channel 554. The medicament entrained in the air is then carried to the lungs of the user.

With a spring 626 having the proper degree of resistance to compression, the movement of the blocking member 546 to open the second inhalation passage 538 occurs at about the same time the user is reaching the desired inhalation rate to carry medicament to the lungs. Thus, the medicament is carried to the user's lung, minimizing deposition in the mouth and throat.

Once the vacuum created by the user's inhalation is no longer greater than the force of the spring 626 on the blocking member 546, the blocking member will be moved distally in the blocking member passage 542 until the blocking member again blocks flow through the second inhalation passage 538. Distal movement of the linear gear 622 causes a counter-clockwise rotation of the vane gear 636, and causes counter clockwise movement of the vane 628 back into the position shown in FIG. 4F.

The user may then open the plunger arm 442 as shown in FIG. 4 and replace the used blister pack. The plunger arm 442 may then be rotated back into the loaded position, and the user is again ready to use the medicament inhalator 400.

Thus there is disclosed an improved dry powder medicament inhalator having an inhalation-activated flow diverting means for triggering delivery of medicament. Those skilled in the art will recognize numerous modifications which may be made without departing from the scope or spirit of the present invention. The appended claims are intended to cover such modifications.

What is claimed is:

1. A dry powder medicament inhalator comprising:
   a housing including a body having:
   a primary inhalation passage extending through the body for allowing airflow through the body;
   a flow restricting member disposed in the primary inhalation passage such that air passing through the primary inhalation passage moves the flow restricting member between a first, nonrestricting position, and a second, restricting position wherein the flow restricting member restricts airflow through the primary inhalation passage;
   a secondary inhalation passage extending at least partially through the body; a blocking member disposed in communication with the second inhalation passage for selectively preventing airflow through the second inhalation passage, the blocking member being moveable between a first, closed position to block airflow through the secondary inhalation passage and a second, open position wherein the blocking member does not prevent airflow through the secondary inhalation passage; and
   a deaggregation channel disposed in fluid communication with the second inhalation passage, the deaggregation channel being configured with at least one impact surface for breaking up aggregations of medicament.

2. The dry powder medicament inhalator of claim 1, wherein the flow restricting member is disposed in communication with the blocking member, such that movement of the flow restricting member into the second position moves the blocking member into the second position, and wherein movement of the blocking member into the first position moves the flow restricting member into the first position.

3. The dry powder medicament inhalator of claim 2, wherein the body has a lower portion with the first passage and the second passage disposed therein, and a separator plate disposed on the lower portion for forming an upper wall of the first inhalation passage and the second inhalation passage, and wherein the flow restricting member and the blocking member are disposed on one side of the separator plate and wherein the gear mechanism is disposed on an opposing side of the separator plate from the flow restricting member and the blocking member.

4. The dry powder medicament inhalator of claim 3, wherein the separator plate has a hole formed therein, and wherein the flow restricting member is attached to the gear mechanism by a shaft extending through the hole in the separator plate.

5. The dry powder medicament inhalator of claim 3, wherein the separator plate has a slot formed therein, and wherein the blocking member is connected to the gear mechanism by a post which extends through and which is slidable along the slot in the separator plate.

6. The dry powder medicament inhalator of claim 5, further comprising a gear mechanism disposed operationally between the flow restricting member and the blocking member.

7. The dry powder medicament inhalator of claim 6, wherein the gear mechanism comprises a circular gear attached to the flow restricting member and a linear gear attached to the blocking member, the linear gear being movable by rotation of the circular gear, and the circular gear being rotatable by linear movement of the linear gear.

8. The dry powder medicament inhalator claim 1, further comprising a spring means disposed in communication with the blocking member for biasing the blocking member into the first position.

9. The dry powder medicament inhalator of claim 1, further comprising a blocking member passage disposed so as to intersect the second inhalation passage, the blocking member being disposed in the blocking member passage.

10. The dry powder medicament inhalator of claim 1, further comprising receptacle means for receiving dry powder medicament.

11. The dry powder medicament inhalator of claim 1, wherein the body comprises a lower cover, an upper cover, a separator plate disposed there between, and a receptacle means disposed in the separator plate.

12. The dry powder medicament inhalator of claim 11, wherein the receptacle means is configured for receiving a blister pack container having a single dose of dry powder medicament.

13. The dry powder medicament inhalator of claim 1, wherein the body comprises a receptacle for receiving a container containing dry powder medicament, and further comprising lancing means for piercing the container.

14. The dry powder medicament inhalator of claim 13, which is the lancing means comprises an arm pivotably attached to the body, the arm being pivotable between a first, reloading position wherein the receptacle is exposed to facilitate placement of a container of medicament in the receptacle, and a second, loaded position wherein the arm covers the receptacle.

15. The dry powder medicament inhalator of claim 14, wherein the arm further comprises a self-resetting lancet disposed in the arm so as to be positioned over the receptacle when the arm is in the second, loaded position.

16. The dry powder medicament inhalator of claim 14, further comprising an airflow channel formed through the arm and disposed in fluid communication with the second inhalation passage when the arm is in the second, loaded position, and when a container in the receptacle has been pierced.

17. The dry powder medicament inhalator of claim 1, further comprising a deaggregation channel disposed in communication with the second inhalation passage, the deaggregation channel being configured with at least one impact surface for breaking up aggregations of medicament.

18. The dry powder medicament inhalator of claim 17, wherein the deaggregation channel is disposed in communication with the first inhalation passage and the second inhalation passage.

19. The dry powder medicament inhalator of claim 17, wherein the deaggregation channel comprises a channel having a zig-zag configuration.

20. The dry powder medicament inhalator of claim 17, wherein the body has a mouthpiece and wherein the deaggregation channel is disposed in fluid communication with the mouthpiece.

21. A medicament inhalator for selectively administering medicament, the medicament inhalator comprising:
   a housing having a body with a proximal end and a distal end;
   a primary inhalation passage extending from the proximal end to the distal end so as to allow air to be drawn into the proximal end and inhaled through the distal end;
   airflow restricting means disposed in the primary inhalation passage for selectively restricting airflow through the primary inhalation passage, the airflow restricting means being movable from a first, nonrestricting position to a second, restricting position wherein the airflow restricting means restricts airflow through the primary inhalation passage, the airflow restricting means being movable into the second position by inhalation through the primary inhalation passage;
   a receptacle for receiving a medicament;
   a secondary inhalation passage extending at least partially through the body and being disposed in fluid communication with the receptacle for receiving medicament from entraining medicament when air is drawn through the secondary inhalation passage;
   a blocking member moveable with respect to the secondary inhalation passage between a first position wherein the blocking member substantially prevents airflow through the secondary inhalation passage and a second position wherein the blocking member allows airflow through the secondary passage; and
   a deaggregation channel having at least one wall against which medicament is impacted to break up aggregations in the mediacement.

22. The medicament inhalator of claim 21, wherein the blocking member and the airflow restricting means are disposed in communication with one another such that inhalation through the primary inhalation passage to move the airflow restricting means into the second position, causes the blocking member to be moved into the second position and allow airflow through the secondary inhalation passage.

23. The medicament inhalator of claim 22, wherein the blocking member is biased into the first position and thereby biases the airflow restricting means into the first position.

24. The medicament inhalator of claim 23, wherein the airflow restricting means comprises a rotatable vane, and wherein the blocking member moves linearly.

25. The medicament inhalator of claim 24, further comprising a gear mechanism disposed in communication with the airflow restricting means and the blocking member such that movement of the airflow restricting means causes movement of the blocking member and movement of the blocking member causes movement of the airflow restricting means such that said blocking member provides a means for selectively moving the blocking member between the first position and the second position.

26. The medicament inhalator of claim 25, wherein the gear mechanism comprises a circular gear disposed in communication with the rotatable vane such that rotation of the rotatable vane rotates the circular gear, and a linear gear attached to the blocking member, the linear gear and the circular gear being disposed in communication such that rotation of the circular gear moves the linear gear and movement of the linear gear rotates the circular gear.

27. The medicament inhalator of claim 21, wherein the primary inhalation passage and the secondary inhalation passage each have a distal end, and wherein the deaggregation channel comprises a deaggregation channel disposed at the distal end of primary inhalation passage and at the distal end of the secondary inhalation passage.

28. The medicament inhalator of claim 27, wherein the deaggregation channel comprises a channel having a zig-zag configuration.

29. The medicament inhalator of claim 21, further comprising an arm pivotably attached to the housing, the arm containing a lancing mechanism positionable above the receptacle to pierce a container of medicament when contained in the receptacle.

30. The medicament inhalator of claim 29, wherein the arm is movable between a first, reload position when medicament can be placed in the receptacle, and a second position, wherein the arm covers the receptacle.

31. The medicament inhalator of claim 30, further comprising an airflow channel passing through the arm so as to be in fluid communication with the second inhalation passage through the receptacle.

32. A method for preventing agglomeration of medicament in an inhalator, the method comprising:
   (a) providing a housing having a body defining a primary inhalation passage and a secondary inhalation passage;
   (b) disposing a blocking member in communication with the secondary inhalation passage such that the blocking member has a first, closed position wherein the blocking member prevents airflow through the secondary inhalation passage, and a second, open position wherein the blocking means does not prevent airflow through the secondary inhalation passage;
   (c) disposing an airflow restricting means in the primary inhalation passage so the airflow restricting means has a first, open position and a second, closed position to selectively inhibit airflow through the primary inhalation passage; and
   (d) disposing a gear mechanism operationally between the flow restricting member and the blocking member such that the movement of the flow restricting member moves the gear mechanism and the gear mechanism moves the blocking member between the first and second positions.

33. The method according to claim 32, wherein the method further comprises disposing the airflow restricting means and the blocking member in communication with one another such that movement of the airflow restricting means from the first, open position to the second, closed position moves the blocking member from the first, closed position into the second open position, and such that movement of the blocking member from the second, open position to the first, closed position moves the airflow restricting means from the second, closed position to the first, open position.

34. The method according to claim 32, wherein the method further comprises biasing the blocking member into the first, closed position.

35. The method according to claim 32, wherein the method further comprises positioning a receptacle for holding a container of medicament in communication with the secondary inhalation passage such that airflow through the secondary inhalation passage entrains medicament from the container of medicament.

36. The method according to claim 35, wherein the method further comprises selectively disposing a lancing means adjacent the receptacle so as to enable piercing of the container of medicament.

37. The method according to claim 36, wherein the method further comprises selectively covering the receptacle with the arm.

38. A method for improving deposition of medicament in the lungs of an inhalator user, the method comprising:
(a) providing a housing having a body defining a primary inhalation passage and a secondary inhalation passage;
(b) positioning an airflow inhibiting means in the primary inhalation passage to selectively restrict airflow through the primary inhalation passage; and
(c) positioning a blocking means in the secondary inhalation passage and connecting the blocking means to the airflow inhibiting means via a gear mechanism so that the airflow means and the blocking means alternatingly inhibit airflow through the primary inhalation passage and the secondary inhalation passage.

39. The method according to claim 38, wherein the method further comprises selectively restricting airflow through the primary inhalation passage to prolong inhalation by the inhalator user while medicament entrained in airflow through the secondary inhalation passage.

40. A method for increasing the deep lung deposition of medicament, the method comprising:
(a) providing an inhalator having a primary inhalation passage, a secondary inhalation passage, medicament in the secondary passage, a movable means for restricting airflow through the primary inhalation passage, and a means for selectively blocking airflow through the secondary inhalation passage;
(b) inhaling through the primary inhalation passage at a first rate;
(c) moving the movalble means for restricting airflow through the primary inhalation passage to restrict airflow through the primary inhalation passage and thereby slow the rate of inhalation through the primary inhalation passage to a second rate; and
(d) unblocking the secondary inhalation passage by rotation of a common gear with the movable means to allow airflow through the secondary inhalation passage and entrainment of the medicament in the airflow through the secondary inhalation passage.

* * * * *

UNITED STATES PATENT AND TRADEMARK OFFICE
CERTIFICATE OF CORRECTION

PATENT NO. : 6,561,186 B2
DATED : May 13, 2003
INVENTOR(S) : Casper et al.

It is certified that error appears in the above-identified patent and that said Letters Patent is hereby corrected as shown below:

Title page,
Item [63], Related U.S. Application Data, currently reads "[62] Division of application No. 09/492,714, filed on Jan. 27, 2000, which is a division of application No. 09/042,656, filed on Mar. 17, 1998, now Pat. No. 6,209,583, which is a continuation-in-part of application No. 08/823,139, filed on Mar. 25, 1997, now Pat. No. 5,823,183, which is a continuation of application No. 08/690,989, filed on Aug, 1, 1996, now Pat. No. 5,692,496." and should read -- [62] Division of application No. 09/492,714, filed on Jan. 27, 2000, which is a division of application No. 09/042,656, filed on Mar. 17, 1998, now Pat. No. 6,209,538, which is a continuation-in-part of application No. 08/823,139, filed on Mar. 25, 1997, now Pat. No. 5,823,183, which is a continuation of application No. 08/690,989, filed on Aug. 1, 1996, now Pat. No. 5,692,496. --

Column 1,
Line 11, currently reads "now U.S. Pat. No. 6,209,583," and should read -- now U.S. Pat. No. 6,209,538, --

Signed and Sealed this

Second Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,561,186 B2
DATED : May 13, 2003
INVENTOR(S) : Casper et al.

It is certified that error appears in the above-identified patent and that said Letters Patent is hereby corrected as shown below:

Title page,
Item [62], Related U.S. Application Data, should read
-- [62] Division of application No. 09/492,714, filed on Jan. 27, 2000, which is a division of application No. 09/042,656, filed on Mar. 17, 1998, now Pat. No. 6,209,538, which is a continuation-in-part of application No. 08/823,139, filed on Mar. 25, 1997, now Pat. No. 5,823,183, which is a continuation of application No. 08/690,989, filed on Aug. 1, 1996, now Pat. No. 5,692,496. --.

Column 1,
Line 11, should read -- now U.S. Pat. No. 6,209,538, --.

Signed and Sealed this

Twenty-eighth Day of February, 2006

JON W. DUDAS
*Director of the United States Patent and Trademark Office*